US00PP35649P2

(12) United States Plant Patent
Meilland

(10) Patent No.: US PP35,649 P2
(45) Date of Patent: Feb. 13, 2024

(54) MINIATURE ROSE PLANT NAMED 'MEIKAPETTE'

(50) Latin Name: *Rosa hybrida*
Varietal Denomination: MEIKAPETTE

(71) Applicant: The Conard Pyle Company, West Grove, PA (US)

(72) Inventor: Alain Antoine Meilland, Antibes (FR)

(73) Assignee: The Conard Pyle Company, West Grove, PA (US)

( * ) Notice: Subject to any disclaimer, the term of this patent is extended or adjusted under 35 U.S.C. 154(b) by 139 days.

(21) Appl. No.: 18/095,712

(22) Filed: Jan. 11, 2023

(51) Int. Cl.
*A01H 5/02* (2018.01)
*A01H 6/74* (2018.01)

(52) U.S. Cl.
USPC ..... Plt./125
CPC ..... *A01H 6/749* (2018.05)

(58) Field of Classification Search
USPC ..... Plt./125
CPC ..... A01H 6/749; A01H 5/02
See application file for complete search history.

(56) References Cited

U.S. PATENT DOCUMENTS

PP16,602 P3 5/2006 Lim et al.
PP18,542 P2 3/2008 Meilland

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEIKAPETTE', is disclosed. The new variety forms attractive, very small double yellow-orange colored flowers. Attractive glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEIKAPETTE'.

STATEMENT REGARDING PRIOR DISCLOSURES BY THE INVENTOR

The first offer for sale of the new variety was Jul. 16, 2022 in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'DELKI' variety (not patented). The male parent (i.e., the pollen parent) of the new variety was the 'BAIpome' variety (U.S. Plant Pat. No. 16,602).

The parentage of the new variety can be summarized as follows:

'DELKI' X 'BAIpome'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms yellow-orange colored flowers,
(b) produces very small double flowers, and
(c) exhibits a green colored glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'DELKI' variety (i.e., seed parent) displays flowers that are striped in color, whereas the new variety displays flowers that are solid in color. In addition, the 'BAIpome' variety (i.e., pollen parent) produces pink colored flowers, whereas the new variety produces yellow-orange colored flowers. Moreover, the new variety can be readily distinguished from other similar non-parental varieties. For example, the 'Meiggili' variety (U.S. Plant Pat. No. 18,542) produces less compact and rounded growth habit compared to the new variety.

The new variety has been named 'MEIKAPETTE'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately two years of age and were observed during July while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of two-years-old specimens of the new variety during July while budded on their own roots and growing outdoors at Le Cannet des Maures, Var, France.

Botantical classification: *Rosa hybrida* cultivar 'MEIKAPETTE'.

Commercial classification: Miniature Rose Plant.

Plant:

*Habit*.—Bushy.

*Height*.—Commonly between 40 cm to 50 cm.

*Width*.—Approximately 50 cm on average.

Branches:

*Color*.—Young stems: commonly near Green Group 143A. Adult wood: commonly near Yellow-Green Group 146A.

*Length*.—From the crown to the flower is typically between 25 cm to 40 cm.

*Diameter*.—Approximately 0.5 cm on average.

*Young shoots*.—Anthocyanin coloration: absent.

*Thorns*.—Configuration on adult stems: curved downwards and elongated on the upper surface and slightly concave on the under surface. Long prickles — quantity: approximately 8 thorns on average per 10 cm long young stem and approximately 16 thorns on average per 10 cm long adult stem. Long prickles — length: approximately 0.3 cm on average on young stems and approximately 0.5 cm on average on adult stems. Long prickles — width: approximately 0.1 cm on average on young stems and approximately 0.1 cm on average on adult stems. Long prickles — base: shape is oval on young stems and on adult stems. Long prickles — color on young stems: commonly near Yellow-Green Group 152C. Long prickles — color on adult stems: commonly near Greyed-Orange Group 164A. Small prickles — quantity: absent.

*Internode*.—Numbers on the entire branch: approximately 10 on average. Length: approximately 2.0 cm on average.

Foliage:

*General appearance*.—Dense with a glossy aspect.

*Number of leaflets*.—3, 5, 7; most often 7.

7 *leaflets leaf*.—Length: typically between 4.9 cm and 6.0 cm on average.

*Terminal leaflet*.—Length: approximately 2.5 cm on average. Width: approximately 1.5 cm on average.

*New foliage*.—Upper surface color: commonly near Green Group 137B. Under surface color: commonly near Green Group 138B. Anthocyanin coloration: absent.

*Adult foliage*.—Upper surface color: commonly near Green Group 139A. Under surface color: commonly near Green Group 139B. Anthocyanin coloration: absent.

Leaflets:

*Shape*.—Tip: cupsidate. Base: rounded.

*Glossiness of upper surface*.—Medium.

*Texture*.—Upper and under surfaces are thick.

*General appearance*.—Oval.

*Serration*.—Small and single.

*Undulation on the margin*.—Weak.

*Venation*.—Color is commonly near Yellow-Green Group 146C and pattern is imparipinnate.

*Petiole rachis*.—Color of upper surface: commonly near Yellow-Green Group 146C. Color of under surface: commonly near Yellow-Green Group 146D. Texture: upper surface is glandular, under surface is smooth with very few prickles. Rachis of terminal leaflet: length is approximately 0.5 cm on average and diameter is typically less than 0.1 cm.

*Petioles*.—Upper surface: no glandular. Under surface: no prickles. Color of upper surface: commonly near Yellow-Green Group 146C. Color of under surface: commonly near Yellow-Green Group 146D. Length: approximately 2.0 cm on average. Diameter: approximately 0.1 cm on average.

*Stipules*.—Length: approximately 0.7 cm on average. Width: approximately 0.2 cm on average. General appearance: narrow. Texture: smooth with glandular edges. Color of upper surface: commonly near Yellow-Green Group 146D. Color of under surface: commonly near Yellow-Green Group 146D.

Inflorescence:

*Number of flowers per stem*.—Typically between 3 to 15 flowers per stem.

*Lastingness of the bloom*.—On the plant: approximately between 7 and 8 days. In vase: not tested.

*Bud*.—Shape: conical. Size: small. Length: approximately 1.0 cm on average. Width: approximately 1.0 cm on average. Color as calyx breaks: upper surface: commonly a color between near Yellow-Orange Group 15B and Yellow-Orange Group 15C margined with a color between Orange Group 28B and Orange Group 28C, basal spot is absent. under surface: commonly a color between near Yellow-Orange Group 15B and Yellow-Orange Group 15C margined with a color between Orange Group 28B and Orange Group 28C, basal spot is absent.

*Sepals*.—Number: commonly 5. Length: approximately 1.2 cm on average. Width: approximately 0.5 cm on average (on median part). Shape: at the top: none elongated. at the base: straight. Extensions: typically 3 sepals with extensions absent or very weak, and 2 sepals with weak extensions. Upper surface: texture: tomentous. color: commonly near Green Group 138C. Under surface: texture: smooth. color: commonly near Yellow-Green Group 146C.

*Receptacle*.—Color: commonly near Yellow-Green Group 146D. Length: approximately 0.4 cm on average. Width: approximately 0.4 cm on average. Surface: smooth. Shape: funnel shaped.

*Peduncle*.—Length: approximately 4.8 cm on average. Width: approximately 0.1 cm on average. Surface: smooth. Color: commonly near Yellow-Green Group 146D.

*Flower*.—Diameter when open: approximately 3.0 cm on average. Shape: cup shaped. Shape when viewed from above: irregular rounded. Type: double. Number of petals under normal conditions: typically between 29 to 33 petals. Petals: shape: obovate (obtuse at the base and rounded at the top). texture: soft. length: approximately 2.2 cm on average. width: approximately 1.7 cm on average. Undulation of the petal: very weak. Reflexing of the petal: strong toward the inside for the most internal petals. Petal incision: very weak. Petal arrangement: imbricated without petaloids. Petal drop: petals drop off cleanly before drying. Fragrance: none. Discoloration of the flower: yes. Color when opening: basal spot on the upper surface: commonly a color between Yellow Group 7A and Yellow Group 7B. upper surface: commonly a color between Yellow-Orange Group 15B and Yellow-Orange Group 15C, margined and suffused with a color between Orange Group 28B and Orange Group 28C. basal spot on the under surface: commonly a color between Yellow Group 7A and Yellow Group 7B. under surface: commonly a color between Yellow-Orange Group 15B and Yellow-Orange Group 15C, margined and suffused with a color between Orange Group 28B and Orange Group 28C. Color of the open flower: basal spot on the upper surface: commonly a color between Yellow Group 7A and Yellow Group 7B. upper surface of the flower: commonly a color between Yellow-Orange Group 15C and Yellow-Orange Group 15D, suffused with near Orange Group 24D. basal spot on the under surface: commonly a color between Yellow Group 7A and Yellow Group 7B. under surface of the flower: commonly near Yellow-Orange Group 14D suffused with near Orange Group 24D. Anthers: number is 36 on average, length is approximately 0.1 cm on average, width is approximately 0.1 cm on average, coloration is commonly near Yellow Group 13A, and arrangement is regular around styles. Filaments: length is approximately 0.2 cm on average and coloration is commonly near Yellow Group 12B. Styles: length is approximately 0.2 cm on average, coloration is commonly near Yellow-Green Group 154D, and number is approximately 22 on average. Stigmas: length is approximately 0.1 cm on average and coloration is commonly near Yellow-Green Group 154D. Pollen: not available at this stage. Hips: does not produce fruit.

Development:

*Vegetation*.—Strong.

*Blooming*.—Early in the season, very abundant and nearly continuous, typically from May to November in France.

*USDA hardiness zone*.—Zone 5 to 9.

*Tolerance to disease*.—Very good, and particularly against Black spot (*Diplocarpon rosae*).

The new 'MEIKAPETTE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIKAPETTE' characterized by the following combination of characteristics:

(a) forms yellow-orange colored flowers, (b) produces very small double flowers, and (c) exhibits a green colored glossy foliage;

substantially as herein shown and described.

* * * * *

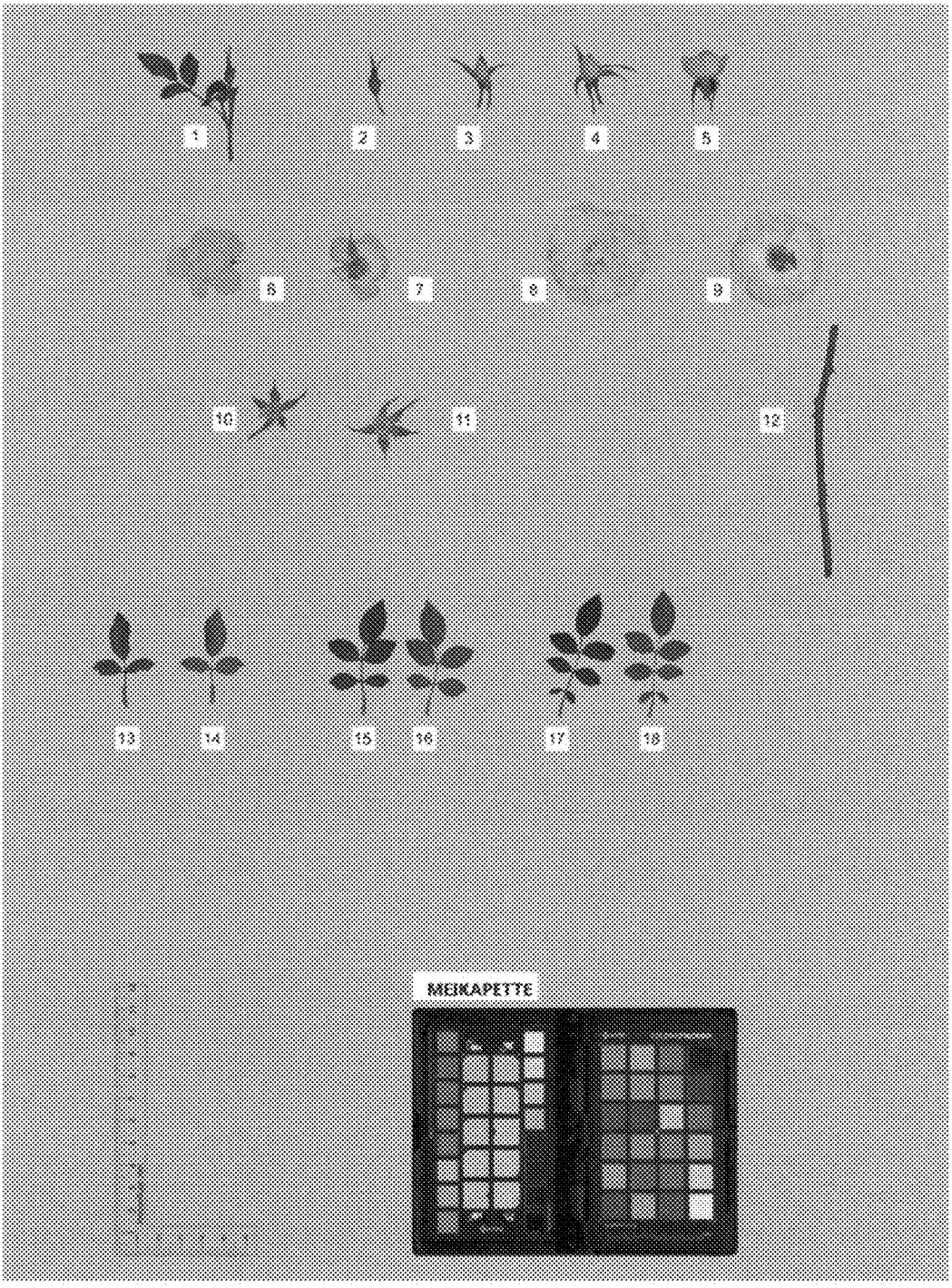
1
2
3
4
5
6
7
8
9
10
11
12
13
14
15
16
17
18
MEIKAPETTE